(12) United States Patent
Toth et al.

(10) Patent No.: US 6,491,670 B1
(45) Date of Patent: Dec. 10, 2002

(54) MINIATURIZED SURGICAL INSTRUMENTS ESPECIALLY USEFUL FOR THE OPTHALMOLOGIC SURGICAL PROCEDURES AND METHODS OF MAKING THE SAME

(75) Inventors: Cynthia A. Toth, Durham, NC (US); Ronald F. Overaker, Durham, NC (US); Brian C. Dodge, Durham, NC (US); Eric A. Postel, Durham, NC (US); Brooks W. McCuen, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/542,985

(22) Filed: Apr. 4, 2000

(51) Int. Cl.[7] ............................................. A61M 5/00
(52) U.S. Cl. ............................................. 604/264
(58) Field of Search ................................. 604/264, 35

(56) References Cited

U.S. PATENT DOCUMENTS

| | | | |
|---|---|---|---|
| 4,047,532 A | | 9/1977 | Phillips et al. |
| 4,204,328 A | | 5/1980 | Kutner |
| 4,445,509 A | | 5/1984 | Auth ........................... 128/305 |
| 4,531,943 A | * | 7/1985 | Van Tassel et al. .......... 604/523 |
| 4,717,387 A | * | 1/1988 | Inoue et al. .................. 604/264 |
| 4,813,926 A | | 3/1989 | Kerwin |
| 4,878,900 A | | 11/1989 | Sundt |
| 5,292,310 A | * | 3/1994 | Yoon ........................... 604/272 |
| 5,358,507 A | | 10/1994 | Daily |
| 5,441,496 A | | 8/1995 | Easley et al. |
| 5,522,826 A | | 6/1996 | Daily |
| 5,603,710 A | | 2/1997 | Easley et al. |
| 5,836,926 A | * | 11/1998 | Peterson et al. ............. 604/264 |
| 5,921,998 A | | 7/1999 | Tano et al. |
| 6,068,641 A | * | 5/2000 | Varsseveld .................. 606/170 |

* cited by examiner

Primary Examiner—Edward K. Look
Assistant Examiner—Michael Leslie
(74) Attorney, Agent, or Firm—Nixon & Vanderhye P.C.

(57) ABSTRACT

Surgical instruments, especially for opthalmological surgical procedures, have a smooth, bulbous arcuate tip that surrounds the distal end of a lumen. The tip may be translucent and flexible. Most preferably, the tip is formed of a compliant, yet self-supporting, material, such as medical grade transparent silicone elastomer. The bulbous arcuate tip may take various geometric forms, for example, generally spherical, ellipsoid or the like. The bulbous arcuate tip may be symmetrical about the elongate axis of the instrument or may be asymmetrical (i.e., angularly disposed) relative to such longitudinal axis. The surgical instruments of this invention are most preferably made by first adhering a length of compliant tubing (e.g., silicone) onto a distal end of a rigid tube (e.g., a section of a stainless steel needle). The proximal rigid tube section is preferably coaxially sleeved over, and affixed to, the distal compliant tube section. A forming wire may then be inserted into the aligned lumens of the proximal rigid tube and distal compliant tube sections so that a terminal end section of the forming wire extends beyond the distal end of the compliant tube section. A bolus of curable liquid elastomer is then applied onto the distal end of compliant tube section around the forming wire protruding therefrom. By rotating and otherwise manipulating the tube sections during curing of the liquid elastomer, a bulbous arcuate tip may be formed. Once the elastomer tip is cured (solidified), the forming wire may be withdrawn thereby forming a through lumen which terminates at the tip. The tip may alternatively be constructed using injection-molding techniques.

10 Claims, 3 Drawing Sheets

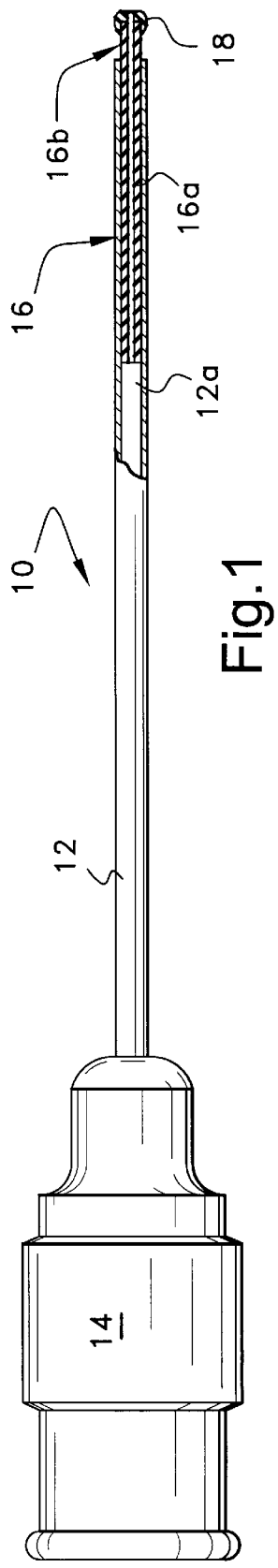
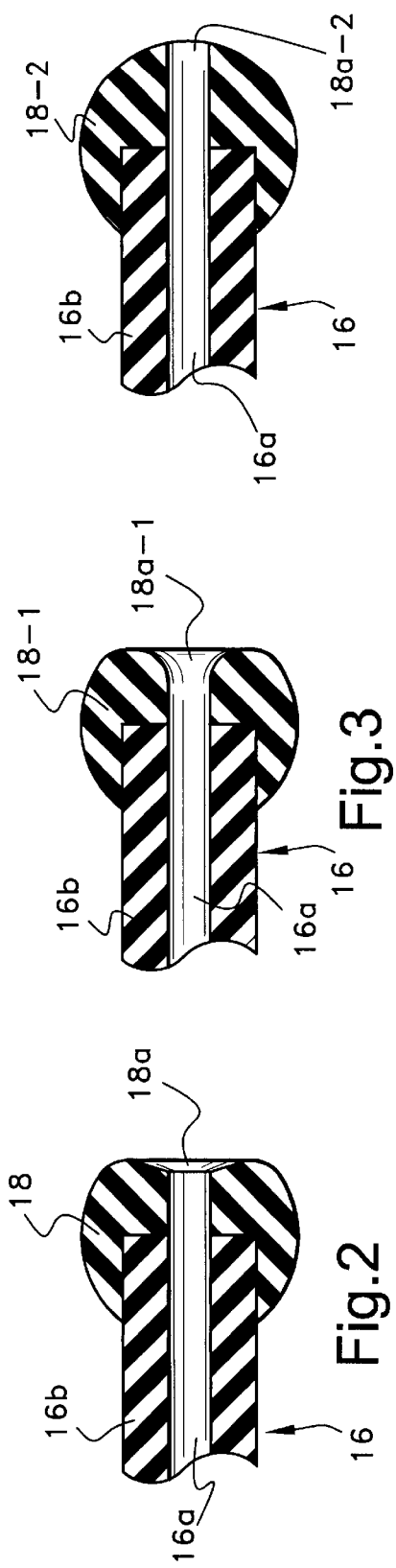
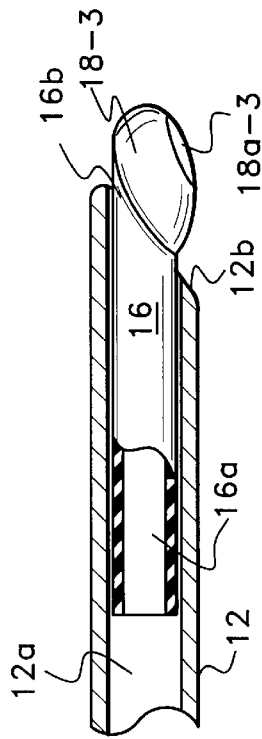

MINIATURIZED SURGICAL INSTRUMENTS ESPECIALLY USEFUL FOR THE OPTHALMOLOGIC SURGICAL PROCEDURES AND METHODS OF MAKING THE SAME

FIELD OF THE INVENTION

The present invention relates generally to the field of surgical instruments, particularly instruments employed in ophthalmologic surgical procedures. In preferred forms, the present invention relates to miniaturized surgical instruments which are especially well suited for ophthalmologic surgical procedures, for example, to aid the surgeon during macular translocation.

BACKGROUND AND SUMMARY OF THE INVENTION

Macular translocation for the treatment of macular degeneration has recently attracted attention as a means to treat age-related macular degeneration. In this regard, and in numerous intraocular surgeries, it is necessary for the surgeon to complete different surgical maneuvers inside the eye such as, stopping bleeding, irrigating or aspirating blood or other fluids or injecting fluid through a retinotomy and using suction to hold tissue to be moved within the eye and fluid flow to release the suction to the tissue. Removing and replacing an intraocular instrument during these maneuvers increases the risk of complications such as retinal tearing or incarceration of detached retina or may allow outflow of fluid during instrument exchange thus increasing the risk of continuation of bleeding. Thus, it is preferred to have an instrument that can perform multiple maneuvers that may be required in sequence.

Therefore, it would be highly desirable if instruments were available that would allow the surgeon to easily and without damage, perform a series of surgical functions, such as, for example, compress bleeding blood vessels while viewing the source of bleeding and extent of tissue blanching from compression, irrigate or aspirate away blood to assist in finding the source of bleeding, irrigate fluid through a hole in the retina while obstructing backflow to create separation of the retina from underlying tissue, securely hold onto retinal or other tissue during attempts to move or otherwise relocate the tissue and then readily release the tissue. It is towards fulfilling such a need that the present invention is directed.

Broadly, the present invention is embodied in surgical instruments having a smooth, bulbous arcuate tip which surrounds a distal end of a lumen. The relative positioning of the lumen and the arcuate tip allow a surgeon to perform a series of surgical functions, such as those identified above. The rounded ball form of the tip associated with the surgical instruments of the present invention prevents abrasion or gouging of adjacent structures as can occur with a typical "squared off" cannula. Most preferably, the tip is formed of a compliant, yet self-supporting, material, such as medical grade transparent silicone elastomer.

The bulbous arcuate tip may take various geometric forms. In this regard, the external surface of the tip is arcuate and thus may be generally spherical, ellipsoid or the like. Also, the bulbous arcuate tip may be symmetrical about the elongate axis of the instrument or may be asymmetrical (i.e., angularly disposed) relative to such longitudinal axis.

The surgical instruments of this invention are most preferably made by first adhering a length of compliant tubing (e.g., silicone) into a distal end of a rigid tube (e.g., a section of a stainless steel needle). Specifically, it is preferred that the proximal rigid tube section is coaxially sleeved over, and affixed to, the distal compliant tube section. A forming wire may then be inserted into the aligned lumens of the proximal rigid tube and distal compliant tube sections so that a terminal end section of the forming wire extends beyond the distal end of the compliant tube section. A bolus of curable liquid elastomer is then applied onto the distal end of compliant tube section around the forming wire protruding therefrom. By rotating or molding and otherwise manipulating the tube sections during curing of the liquid elastomer, a bulbous arcuate tip may be formed. Once the elastomer tip is cured, the forming wire or mold may be withdrawn thereby forming a small hollow bore lumen which terminates at the tip. That is, the bulbous arcuate tip will surround the distal end of the thus formed lumen.

These and other aspects and advantages of the present invention will become more clear from the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein, FIG. 1 is a side elevation view, partly sectioned, showing one exemplary embodiment of a surgical instrument according to the present invention;

FIG. 2 is an enlarged cross-sectional view of the bulbous arcuate tip employed in the surgical instrument of FIG. 1;

FIG. 3 is an enlarged cross-sectional view of another embodiment of a bulbous arcuate tip that may be employed in the surgical instruments of this invention;

FIG. 4 is an enlarged cross-sectional view of yet another embodiment of a bulbous arcuate tip that may be employed in the surgical instruments of this invention;

FIG. 5 is an enlarged view, partly sectioned, of yet another embodiment of a bulbous arcuate tip that may be employed in the surgical instruments of this invention;

DETAILED DESCRIPTION OF THE INVENTION

Figure 6:
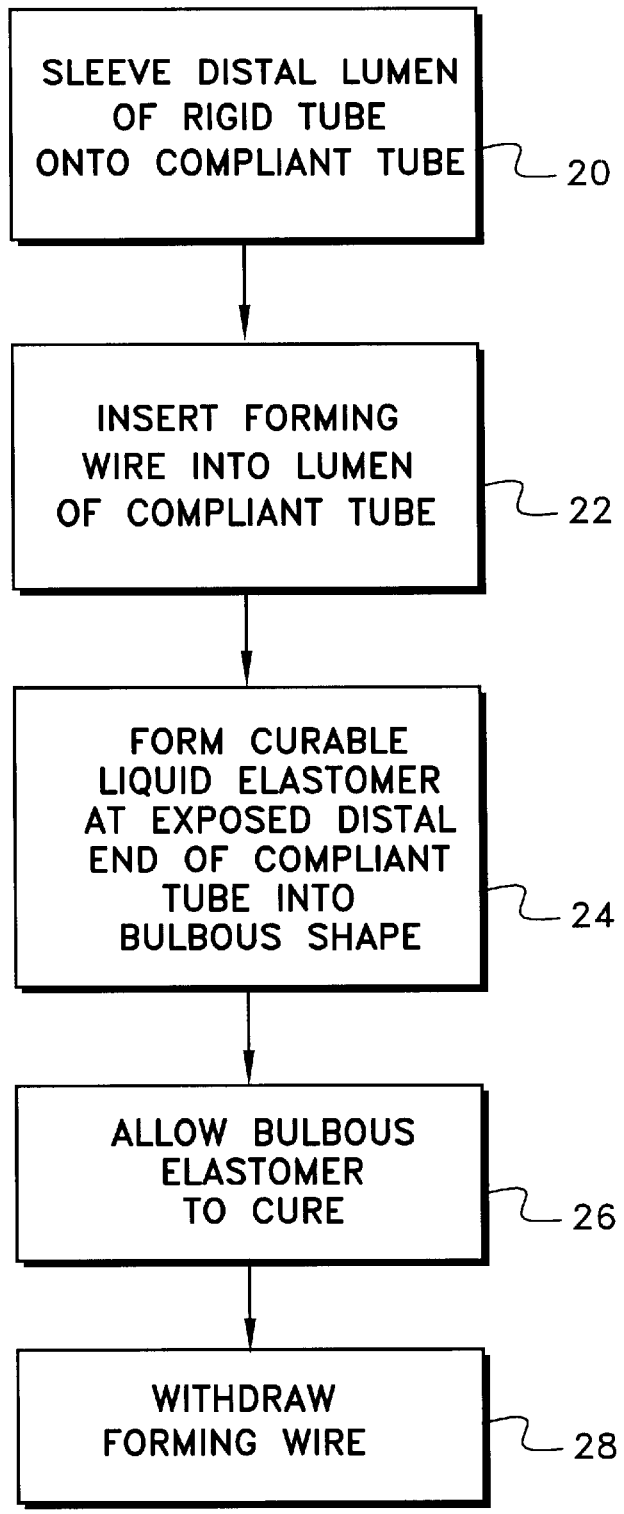
FIG. 6 is a schematic diagram showing the process steps that may be employed to produce the surgical instruments of this invention.

Accompanying FIG. 1 shows one preferred embodiment of a surgical instrument 10 according to the present invention. In this regard, the instrument 10 includes a rigid stainless steel tube section 12 extending from a proximal coupling member 14. The rigid tube section 12 is most preferably formed from a section of a standard medical needle, such as a 19 gauge stainless steel needle. The coupling member 14 is in and of itself conventional and can be a Luer-type or other suitable locking mechanism to allow the instrument 10 to be connected to a vacuum source, for example.

A compliant tube section 16 most preferably formed of a silicone elastomer is adhered within the lumen 12a of the rigid tube section 12, most preferably using a curable silicone elastomer adhesive. The rigid tube section 12 is sleeved over the compliant tube section 16 is positioned so that each of the lumens 12a, 16a, respectively, is aligned coaxially with one another. Also, as can be seen, a distal end portion 16b of the compliant tube section 16 extends distally from the rigid tube section 12.

A solid bulbous arcuate tip 18 is adhered integrally to the distal end portion 16b of compliant tube section 16. The tip 18 thus has a diameter which is greater than the diameter of the compliant tube section 16. Most preferably, the arcuate tip 18 is a cured medical grade silicone elastomer, such as the curable silicone elastomer product # MD-4211, that is available commercially from NuSil Technology of Carpinteria, Calif. As can perhaps be seen more clearly in accompanying FIG. 2, the external surface of the tip 18 has a smooth, substantially spherical cross-sectional geometry. A distal-most section of the tip 18 is truncated so as to form a generally conical recessed, reentrant port 18a which communicates with the lumen 16a of the compliant tube section.

The lumen communication port 18a may, however, take other forms, such as the convexly curved horn-shaped lumen communication port 18a-1 associated with the tip 18-1 depicted in accompanying FIG. 3. Alternatively, no reentrant geometry needs to be provided, for example, as depicted in the generally spherical tip 18-2 shown in accompanying FIG. 4, in which case the lumen communication port 18a-2 simply opens onto the spherical external surface at a distal-most location thereof.

It will be observed that the tips 18, 18-1 and 18-2 each symmetrically surround the lumen 16a of the distal end portion 16b of the compliant tube section 16. However, tips that are asymmetrical relative to the lumen axis are also contemplated as shown by the embodiment depicted in accompanying FIG. 5. As shown, the tip 18-3 is smoothly arcuate similar to the tips 18, 18-1 and 18-2 described previously, but is disposed asymmetrical relative to the lumens 12a and 16a of the rigid and compliant tube sections 12 and 16, respectively. As such, the communication port 18a-3 is positioned at an angle (preferably an obtuse angle) relative to the lumen 16a of compliant tube section 16. In the embodiment depicted in FIG. 5, the distal face 12b of the proximal rigid tube section 12 is angled so that it is substantially perpendicular to the axis of the communication port 18a-3 and thereby provide lateral structural support for the tip 18.

An exemplary process for making the surgical instruments of the present invention is depicted schematically in accompanying FIG. 6. In this regard, the rigid tubular section 12 may initially be cut, for example, from a standard 19 ga. stainless steel needle. The compliant tube section 16 may then, in step 20, be inserted into the lumen 12a of the proximal rigid tube section 12 and joined thereto by means of any suitable medical grade adhesive. For example, when using a silicone tube for the compliant tube section 16, a curable silicone adhesive may advantageously be employed for such purpose.

Once the sleeved rigid and compliant tube sections 12, 16, are joined axially one to one another, a forming wire may be inserted into and through their axially aligned lumens 12a, 16a, respectively, as shown schematically in step 22. In this regard, the forming wire is positioned so that its distalmost end section extends beyond the distal end of the compliant tube section.

A bolus of a curable liquid elastomer, for example, a curable silicone elastomer, may then be applied in step 24 onto the distal end of the compliant tube section around the protruding distalmost end section of the forming wire. The viscosity of the liquid elastomer in the blended but uncured state should be between about 40,000 to about 70,000 cP, which is appropriate to allow it to be shaped by suitable manipulation of the joined rigid and compliant tube sections 12, 16 against gravity forces while yet being sufficiently low to permit the elastomer to flow somewhat, and thereby be shaped, during curing according to step 26. Advantageously, the viscosity of the liquid elastomer may be between about 70,000 cP to about 150,000 cP after a two hour period of rest. For example, when using a curable liquid silicone elastomer, its viscosity should be about 100,000 cP after a two hour rest period.

The bolus of liquid curable elastomeric material is applied in an amount sufficient to achieve the desired final nominal diameter of the arcuate tip. Most preferably, the solidified arcuate tip is relatively miniaturized—that is, has a nominal diameter of less than about 0.80 mm, and typically greater than about 0.75 mm. Preferred arcuate tips according to the present invention will thus be generally spherically shaped with a nominal diameter of between about 0.75 mm to about 0.80 mm which is larger than the diameter of the compliant tubing to which the tip is affixed.

The reentrant sections, if needed, can be made by injection molding or by allowing an initial "skin" layer to be formed during curing of the bolus of liquid elastomer. Once this cured "skin" layer is formed, the forming wire may be withdrawn slightly and/or rotated within the aligned lumens 12a, 16a to thereby cause the cured skin layer to be likewise withdrawn and/or rotated slightly relative to the remaining uncured portion of the liquid elastomer bolus. Once the desired reentrant geometry is achieved by manipulation of the forming wire, the remaining bolus of liquid elastomer is allowed to cure in step 26. Once cured, the forming wire may be withdrawn in step 28 completely from the lumens 12a, 16a thereby exposing the lumen communication port of the arcuate tip.

Figure 7:
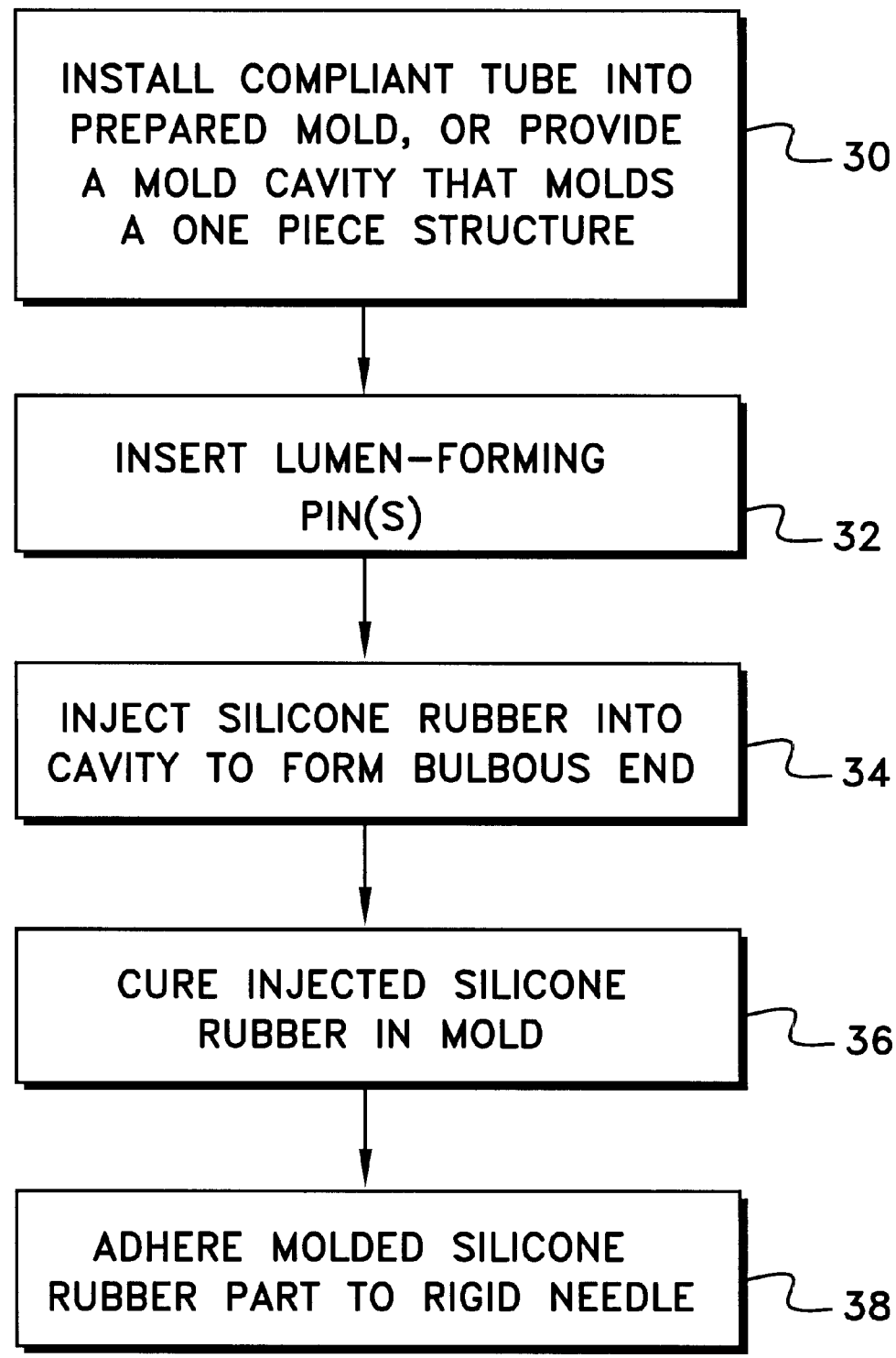
FIG. 7 is a schematic diagram showing the process steps that may be employed to produce the surgical instruments of this invention by injection molding.

As noted briefly above, the surgical instruments of this invention can conveniently be made by injection molding, for example, using the techniques depicted generally in accompanying FIG. 7. In this regard, in step 30, the compliant tube may be initially positioned within a suitably shaped mold cavity (i.e., one having the desired arcuately bulbous shaped mold cavity to form the distal tip as shown in FIGS. 1–5). Alternatively, if a one-piece structure (i.e., one having the compliant tube and the bulbous arcuate tip formed as one piece) is desired, then a conformably shaped mold cavity is provided. In either situation, one (or more) lumen-forming pins which have the desired diameter may be inserted into the mold in step 32 to ultimately form the lumen of the instrument.

Thereafter, in step 34, liquid silicone rubber having the viscosity as noted previously may be injected into the mold cavity to either form the bulbous arcuate tip integrally with the compliant tube, or form both the compliant tube and the tip as a one-piece structure. The injected silicone rubber is then allow to cure in the mold in step 36 until it is self-supporting, at which time the mold is opened and the injection molded part removed. Following removal of the lumen-forming pin, the injection molded part may be adhered to the distal end of the rigid needle in step 38 using a suitable adhesive.

The present invention will be further understood from the following Example, which is intended to be explanatory only, and non-limiting with respect thereto.

EXAMPLES

A standard 19 ga. stainless steel (SS) needle was used and cut to obtain a section having a length of 29.75 mm. The end of the cut needle was de-burred so as to be smooth. The needle section was then cleaned ultrasonically to remove any contaminants that might be present. A 1 cm length of silicone tubing (0.635 mm od×0.3 mm id) was ultrasonically cleaned, and wetted on its exterior surface with the MD-4211. A 1–10 ratio of hardner to silicone elastomer was required for the MD-4211. In order to achieve good adhesion, the silicone tube was moved axially in and out of the rigid SS needle to ensure that its exterior surface was covered adequately with the liquid curable silicone elastomer. Just prior to curing, excess liquid silicone elastomer was wiped off the end section of the silicone tube that extended distally beyond the terminal end of the SS needle section by about 0.8 mm. Once the silicone tube has been positioned correctly relative to the rigid SS tube, and the excess liquid removed from the protruding distal section, the curable liquid silicone was cured by, gently heating with a hot air gun.

Once cured, the silicone tube was affixed to the rigid SS tube with the lumens of each tube being axially aligned with one another. A polished forming wire having a nominal outside diameter of 0.2 mm was inserted into and through the aligned lumens of the joined rigid SS and silicone tube sections so that about 1 cm extends beyond the terminal distal end of the silicone tube.

A silicone elastomer was prepared by mixing as stated above. Using a measuring reticule in a microscope, a bolus of the liquid silicone elastomer sufficient to form a ball of no more than about 0.75 mm in diameter was placed onto the exposed distal end of the silicone tube around the protruding forming wire. The distalmost end of the silicone tube was positioned so it was approximately at the center of the bolus of liquid silicone. The tubes were rotated against gravity forces so as to cause a generally spherical tip to form. Capillary action caused a sufficient amount of the liquid silicone elastomer to be drawn into the distalmost end of the silicone tube lumen thereby ensuring integral connection therebetween.

Following application of the bolus of liquid silicone material and initial shaping thereof, the liquid silicone material was allowed to initially cure somewhat to an extent that a solidified "skin" formed on its external surfaces. A variety of tip shapes as shown in drawing FIGS. 1–4 were made by relative movement of the forming wire and the joined rigid and silicone tube sections. Once the desired tip shape was obtained, the bare terminal end section of the forming wire was positionally fixed to maintain the tip shape during final curing and solidification. After the ball was correctly shaped, the silicone rubber was slowly raised to approximately 250° C. This final cure required approximately 3 minutes to complete.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An ophthalmic surgical instrument comprising a proximal rigid metal tube section, an elastomeric compliant tube section sleeved within and immovably fixed to said rigid metal tube section so as to establish a lengthwise extending lumen, said compliant tube section having a distal portion which extends distally beyond said rigid metal tube section, and a self-supporting solid bulbous elastomeric tip joined to said distal portion of said compliant tube section, said tip having a port which communicates with said lumen and being arcuately shaped with a nominal diameter larger than a diameter of the compliant tube section, and wherein said tip is formed of an elastomeric material which is translucent or transparent.

2. The surgical instrument of claim 1, wherein the lumen-communication port is axially aligned with the lumen.

3. The surgical instrument of claim 1, wherein the lumen-communication port is angularly oriented relative to the lumen.

4. The surgical instrument of claim 1, wherein the lumen-communication is recessed into said tip.

5. The surgical instrument of claim 4, wherein said recessed lumen-communication port is generally truncated conically shaped in cross-section.

6. The surgical instrument of claim 4, wherein said recessed lumen-communication port is generally horn-shaped in cross-section.

7. The surgical instrument of claim 1, wherein said compliant tube section is also formed of said elastomeric material which is translucent or transparent.

8. The surgical instrument of claim 1 or 7, wherein said elastomeric material is a translucent or transparent silicone elastomer.

9. The surgical instrument of claim 1, wherein the nominal diameter of the tip is less than 0.80 mm.

10. The surgical instrument of claim 9, wherein the nominal diameter of the tip is between about 0.75 mm to about 0.80 mm.

* * * * *